United States Patent [19]

Peyman

[11] Patent Number: 5,560,356
[45] Date of Patent: Oct. 1, 1996

[54] DIAGNOSTIC SYSTEM AND METHOD USING AN IMPLANTED REFLECTIVE DEVICE

[75] Inventor: Gholam A. Peyman, New Orleans, La.

[73] Assignee: Vitrophage, Inc., Lyons, Ill.

[21] Appl. No.: 352,562

[22] Filed: Dec. 9, 1994

Related U.S. Application Data

[63] Continuation-in-part of Ser. No. 200,348, Feb. 23, 1994, abandoned.

[51] Int. Cl.$^6$ ...................................................... A61B 6/00
[52] U.S. Cl. ........................ 128/633; 128/653.1; 128/664; 128/899
[58] Field of Search ..................... 128/632–634, 128/664, 665, 666, 653.1, 899

[56] References Cited

U.S. PATENT DOCUMENTS

| | | | |
|---|---|---|---|
| 3,958,560 | 5/1976 | March | 128/633 |
| 3,963,019 | 6/1976 | Quandt | 128/633 |
| 4,073,292 | 2/1978 | Edelman . | |
| 4,138,998 | 2/1979 | Nowogrodzki | 128/653.1 |
| 4,233,964 | 11/1980 | Jefferts et al. . | |
| 4,597,392 | 7/1986 | Opitz et al. . | |
| 4,606,351 | 8/1986 | Lubbers | 128/665 |
| 4,622,974 | 11/1986 | Coleman et al. | 128/634 |
| 4,680,268 | 7/1987 | Clark, Jr. . | |
| 4,882,492 | 11/1989 | Schlager . | |
| 4,889,407 | 12/1989 | Markle et al. . | |
| 5,000,901 | 3/1991 | Iyer et al. | 128/634 |
| 5,009,230 | 4/1991 | Hutchinson . | |
| 5,127,077 | 6/1992 | Iyer et al. . | |
| 5,193,544 | 3/1993 | Jaffe . | |
| 5,209,231 | 5/1993 | Cote et al. | 128/633 |

OTHER PUBLICATIONS

*Noninvasive Glucose Monitoring of the Aqueous Humor of the Eye: Part I. Measurement of Very Small Optial Rotations* by B. Rabinovitch, W. F. March and Robert L. Adams, Published in *Diabetes Care*, vol. 5 No. 3 May–Jun. 1982.

*Noninvasive Glucose Monitoring of the Aqueous Humor of the Eye: Part II. Animal Studies and the Scleral Lens* by Wayne F. March, B. Rabinovitch and Robert L. Adams, Published in *Diabetes Care*, vol. 5, No. 3 May–Jun. 1982.

*Primary Examiner*—Ruth S. Smith
*Attorney, Agent, or Firm*—Roylance, Abrams, Berdo & Goodman, L.L.P.

[57] ABSTRACT

A device and method for testing an animal for the existence of a biomedical disorder or condition, such as the presence or concentration of particular compositions or hyperglycemia/hypoglycemia, is disclosed comprising a radiant energy source [12] a reflective device [14] implanted within the body [16] of an animal test subject, and a receiver system [18] to receive the beam of reflected radiant energy for use in determining the existence of the biomedical disorder or condition.

19 Claims, 2 Drawing Sheets

DIAGNOSTIC SYSTEM AND METHOD USING AN IMPLANTED REFLECTIVE DEVICE

This is a continuation-in-part of Ser. No. 08/200,348 filed Feb. 23, 1994, with the United States Patent and Trademark Office now abandoned.

FIELD OF THE INVENTION

The present invention relates generally to devices and methods for testing an animal for the existence of a biomedical disorder or condition and more particularly to a system for testing an animal for the existence of a biomedical disorder or condition, such as hyperglycemia or hypoglycemia, using radiant energy reflected off an implanted reflective device.

BACKGROUND OF THE INVENTION

Many medical diagnostic techniques project radiant energy into the body of an animal for testing for the existence of a biomedical disorder or condition. For example, the integrity of the skeletal structure may be examined by passing X-rays through the body. The dense bony material substantially blocks the passage of the X-rays, permitting a doctor or other medical care provider to visually inspect for fractures or other defects in the skeletal structure.

X-rays are also used in mammography to detect tumors in the breast. In this technique, the X-rays are passed through the breast such that they do not travel through any bony structure. The X-rays are hindered by tumors in the breast which show up as dark spots on the X-ray film. Although under this technique tumors may be detected earlier than by physical examination, the technique is difficult to administer due to the angle that the X-rays must be passed through the breast.

To examine the soft tissue of the body, other techniques are available. These include, among others, CAT scans and magnetic resonance imaging. Both project radiant energy onto the body for obtaining information about the physical structure of the body. Although these techniques are highly accurate and provide detailed information, they are time consuming to administer and costly to perform.

Further, measurement of the level of certain chemicals or compositions within the body is a diagnostic test of particular interest. Radiant energy may be used in these applications as passage of the radiant energy through particular chemicals or compositions often alters the radiant energy in a manner that can be measured and analyzed. For example, the monitoring of the glucose level of the blood is of particular importance to diabetics. One method of measuring the person's glucose involves projecting polarized radiation onto the body and measuring the optical rotation of the radiation that passes through the body. This optical rotation corresponds to the concentration of the glucose within the body. To be effective, however, the radiation must be passed through a relatively thin area of the body. Thus, the technique is usually performed on a person's earlobes or fingers. However, the skin and other tissue through which the radiant energy passes can interfere with the accuracy of the test.

To overcome the inaccuracies associated with passing the radiant energy through the tissue, attempts have been made to project the radiant energy through the cornea and aqueous humor of the eye. This is done because the concentration of glucose and oxygen in the cornea and aqueous humor, for example, reflects the concentration generally throughout the body. However, several problems are associated with this technique as well. For example, in Quandt U.S. Pat. No. 3,963,019, radiant energy is projected into the eye and reflected off the iris. The reflected radiation is detected and the optical rotation caused by passage of the reflected radiation through the cornea and aqueous humor is determined. However, this method suffers from poor sensitivity, in part because it relies on reflecting the radiant energy off the iris. Other attempts, as shown in March U.S. Pat. No. 3,958,560 and March U.S. Pat. No. 4,014,321, project the radiant energy at a shallow angle into the cornea on one side of the eye, through the aqueous humor, and out the cornea on the opposing side of the eye. Although this test is able to achieve high accuracy, it is difficult to administer because of the shallow angle at which the radiant energy must be passed through the eye.

Thus, there has been a considerable need for a relatively inexpensive device and method for reliably and easily performing tests using radiant energy for detecting the existence of biomedical disorders or conditions. More particularly, there has been a considerable need for a device and method for reliably and easily measuring the level of a substance in the body using radiant energy.

SUMMARY OF THE INVENTION

The present invention provides a system adapted to easily and reliably permit the testing for the existence of a biomedical disorder or condition using radiant energy. To this end, and in accordance with the principles of the present invention, a radiant energy source, reflective implanted device, and a receiver including a processor are provided that cooperate to gather information for a doctor or other medical care provider for use in determining the existence of a biomedical disorder or condition. The radiant energy source is positioned to project incident radiation into a portion of the body of an animal test subject. This incident radiation is reflected off the implanted reflective device and back out of the body. The receiver is positioned to detect the radiation and the processor calculates changes in the reflected radiation, thereby providing information for use in determining the existence of the disorder or condition for which the test is being administered.

The implanted reflective device is a mirror having a length and width of from about 10 micrometers to about 3 millimeters and the incident radiation is preferably a polarized beam of radiation or near-infrared radiation, Further, it is contemplated that the system will be particularly suitable for use in measuring the glucose level of an animal by implanting the reflective device within the anterior chamber or cornea of the eye, In this aspect of the invention, radiant energy is projected through the aqueous humor and/or cornea of the eye. The radiant energy is reflected off the implanted mirror and passes back through the cornea or back through the cornea and aqueous humor depending on where the mirror is implanted in the eye. The receiver then detects the reflected radiation and a processor calculates the optical rotation of the reflected radiation, thereby providing the glucose concentration in the aqueous humor and/or cornea. In this aspect of the invention, the mirror is preferably implanted in either the iris or the corneal stroma of the eye.

Alternatively, the incident radiation may be near-infrared radiation. The near-infrared radiation is projected into the body, reflected by the implanted reflective device, and detected by the receiver. The detected radiation is then processed to measure the absorption and/or reflectance of the various wave lengths of radiation in the near-infrared spectral region. These measurements may be used to determine the concentration of various compositions in the body. In turn, this can be used to diagnose the existence of various biomedical conditions or disorders.

By virtue of the foregoing there is thus provided a relatively inexpensive device and method for quickly and reliably testing for the existence of a biomedical disorder or condition using radiant energy. More particularly, there is provided a device and method for quickly and reliably determining the glucose level of the test subject. These and other objects and advantages of the present invention shall be apparent from the accompanying drawings and the description thereof.

BRIEF DESCRIPTION OF THE DRAWINGS

The accompanying drawings, which are incorporated in and constitute a part of this specification, illustrate embodiments of the invention and, together with a detailed description of the invention given below, serve to explain the principles of the present invention.

DETAILED DESCRIPTION OF THE INVENTION

Figure 1:
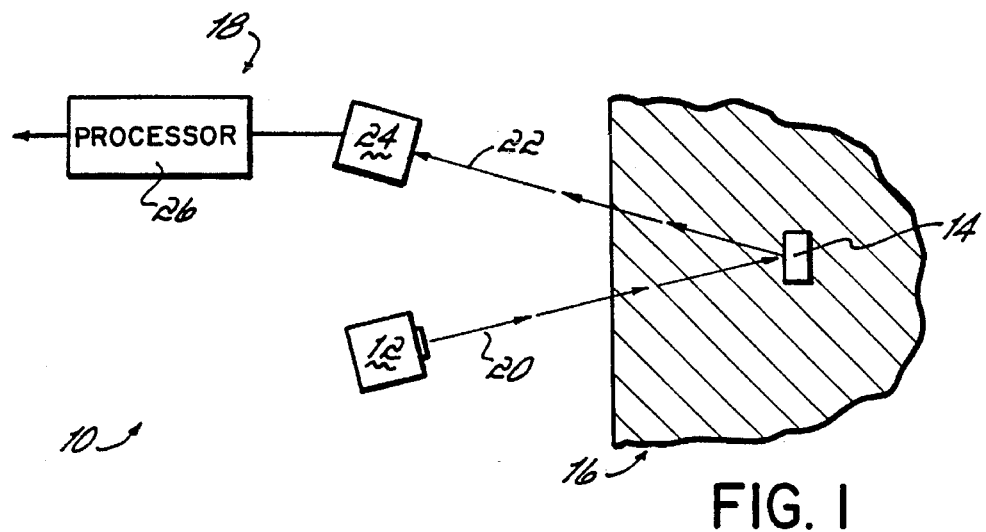
FIG. 1 is a schematic diagram illustrating the major components of a diagnostic system using radiant energy and an implanted reflective device in accordance with the principles of the present invention.

With reference to FIG. 1, there is shown a diagnostic system 10 comprising a radiant energy source 12, a reflective device 14 that is implanted within the body 16 of an animal test subject, and a receiver system 18, Radiant energy source 12 is positioned to project a beam of incident radiant energy 20, such as near-infrared radiation or a polarized beam of radiation, into the body 16 of the animal test subject, which is reflected off reflective device 14, The reflected beam 22 of radiant energy travels back through body 16 and is received by receiver system 18, which comprises a detector 24 and a processor 26. Detector 24 is positioned to detect the reflected radiation, which is processed by processor 26 to provide information regarding changes to incident radiant energy 20 as a result of passing through body 16. This information may then be displayed or further processed to generate information for a doctor or other medical care provider regarding the biomedical disorder or condition for which the test is being administered.

Radiant energy source 12 may be any suitable device capable of producing radiant energy for use in diagnostic testing. All that is required is that the radiant energy be of a type that is altered by the passage through the body such that the particular biomedical condition or disorder may be detected. For example, many types of radiant energy satisfy this criteria, such as polarized radiant energy or near-infrared radiant energy. As will be discussed below, both of these types of radiant energy are altered by passage through certain chemicals or compositions in a manner that can be detected and processed such that the concentration of the chemical or composition may be determined. The types of compositions or compounds that may be detected by the present invention include collagen, elastin, iron, cholesterol, beta-carotene, electrolytes, proteins, and calcium. This list is not exclusive and other compounds or compositions, the present and concentration of which may be readily determined by use of the present invention, will be readily apparent to those skilled in the art.

The presence or concentration of these various compounds in the body, such as, by way of example, glucose, may reflect a specific medical condition or disorder, such a hyperglycemia or hypoglycemia. Similarly, the level of iron may reflect anemia and cholesterol an increased risk of heart disease, As will be readily apparent to those skilled in the art, other types of radiant energy are available, both in the visible range and invisible range, that possess the same or similar characteristics and may be used without departing from the spirit or scope of the present invention. Moreover, the concentration or presence of other compounds as evidencing a medical condition or disorder will also be readily apparent.

Figure 2:
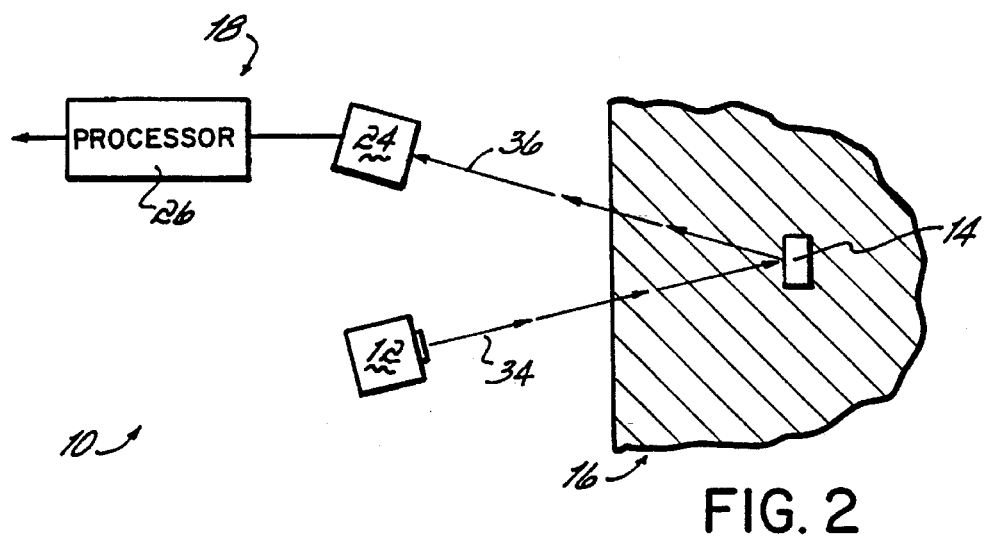
FIG. 2 is a schematic view of a diagnostic system in accordance with the principles of the present invention using near-infrared radiation.

With reference to FIG. 2, there is shown an embodiment of the present invention wherein near-infrared radiation is used in diagnostic system 10. In this application, radiant energy source 12 produces near-infrared radiation, which is radiation in the band of wavelengths between about 0.7 micrometers and about 2–3 micrometers. As described in Jolanta Soos, *Industrial Process Monitoring Requires Rugged Tools,* Laser Focus World, August, 1994, at 87 (hereinafter "the Laser Focus World article"), a beam of near-infrared radiation may be generated by an acousto-optic tunable filter (AOTF), solid-state wavelength-tuning device. An AOTF is an optical crystal, such as one specially prepared from quartz or tellurium oxide, having a high frequency transducer attached to one side. The transducer produces a radio frequency which interacts with light waves passed through the crystal such that the crystal acts as a narrow-line band-pass filter. Accordingly, at any given applied radio frequency, the AOTF transmits only a single wavelength of light. By quickly tuning the radio source to different frequencies, near-infrared radiation having a number of precisely known wavelengths is generated.

As many compositions or chemicals exhibit absorption bands within the near-infrared radiation spectral region, the presence and/or concentration of these compositions or chemicals in a sample may be determined by passing near-infrared radiation, at a number of precisely known wavelengths, through the sample and measuring the absorption and/or reflectance of the wavelengths of the radiation that have passed through the sample.

In the present invention, radiation source 12, such as described above, is positioned to project a beam of incident near-infrared radiation 34 into a portion of the body 16 of a patient at a location for which the presentation or concentration of a particular substance or compound is to be determined. Reflective device 14, which is configured and sized to be implanted in the body 16 of a patient, is positioned within the body 16 to reflect outwardly the incident radiation 34. For example, reflective device 14 could be implanted in a leg, torso, eye, or any other suitable location. Detector 24, in turn, is positioned to detect the reflected radiation 36. The detected signal is processed by processor 26 to determine the absorption and/or reflectance of each wavelength of near-infrared radiation in the detected signal.

As discussed in the Laser Focus World article, specially developed software relying on chemometrics may be used in processor 26 to determine the concentration of various compounds based upon the strength of the wavelengths received by detector 24. Under this method, samples having a range of known compositions are presented to diagnostic system 10 prior to use for correlation by the software in processor 26. From the baseline information, the software generates algorithms for calculating the composition or concentration information from the detected signals during actual use.

It has been found advantageous to use a mirror for reflective device 14. This has the advantage of being biocompatible and inexpensive. Further, it is an efficient device for reflecting radiant energy. The mirror may be any suitable size, however, it has been found preferable to limit the size of the mirror in length and width to from about 100 micrometers to about 1 centimeter for this application. Additionally, as will be readily apparent to those skilled in the art, multiple mirrors 14 may be implanted simultaneously in any number of locations in the body. Moreover, if the length and width of the mirror are limited to about 100 micrometers, mirrors 14 may be injected through a needle into the desired location within the body 16 of the patient.

Figure 3:
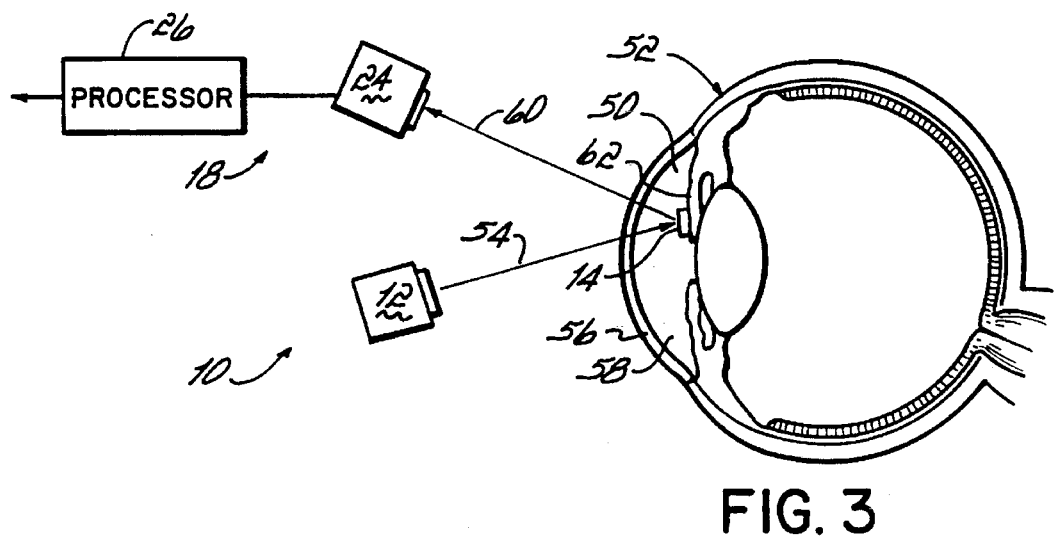
FIG. 3 is a schematic view of the diagnostic system of FIG. 1 with the reflective device implanted in the iris of an eye.
Figure 4:
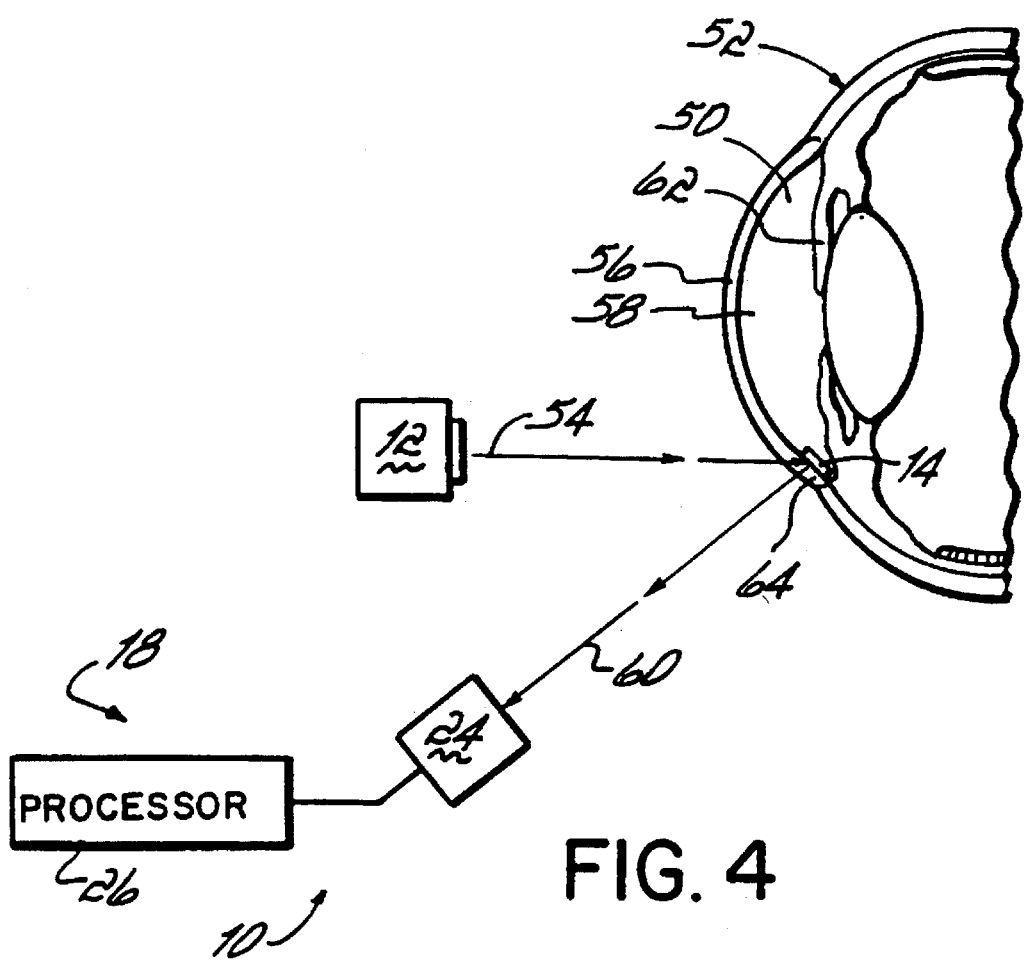
FIG. 4 is a schematic view of a diagnostic system of FIG. 1 with the reflective device implanted in the corneal stroma of an eye.

With reference to FIGS. 3 and 4, there is shown an alternative embodiment of the present invention particularly adapted to measure the concentration of glucose or other substance within the body. To this end, reflective device 14 is configured and sized to be implanted within the anterior chamber 50 or cornea 56 of an eye 52. A polarized beam of radiation 54, to be reflected of reflective device 14, is projected into the eye by radiant energy source 12, which is preferably a polarizing crystal or other appropriate device. If reflective device 14 is implanted in the anterior chamber 50 (see FIG. 3), polarized beam 54 travels through the cornea 56 and aqueous humor 58, is reflected off reflective device 14, and the reflected beam 60 travels back through the aqueous humor 58 and cornea 56. Alternatively, if reflective device 14 is implanted in the cornea 56 (see FIG. 4), polarized beam 54 travels through the cornea 56, is reflected off reflective device 14, and the reflected beam 60 travels back through the cornea 56, As polarized beam 54 travels through the aqueous humor 58 and/or cornea 56, the polarized beam is refracted or optically rotated an amount that is proportional to the concentration of glucose or other substance within the aqueous humor and/or cornea. In either event, receiver system 18 is positioned to receive reflected radiation 60. To this end, detector 24 detects the reflected beam 60 and its corresponding refraction or optical rotation. In turn, processor 26 calculates the optical rotation or refraction of reflected beam 60 in comparison with incident polarized beam 54. Based upon this optical rotation or refraction, processor 26 may then calculate the concentration of glucose or other substance of the aqueous humor and/or cornea. Additionally, as will be readily appreciated by those skilled in the art, the signal detected by receiver system 18 may be processed independently of receiver system 18 and at a remote location.

Detector 24 advantageously comprises a polarizing crystal similar to that used in radiant energy source 12, however, any suitable detector may be used.

Reflective device 14 may be implanted within anterior chamber 50 using any standard technique known to those skilled in the art, such as through the back or the side of the eye or, if reflective device 14 is small enough, by injection through a needle through the side of the cornea. Additionally, reflective device 14 may be implanted within any location in the anterior chamber of the eye, so long as polarized beam 54 travels through the aqueous humor 58 prior to being reflected off reflective device 14. To this end, it has been found beneficial to implant reflective device 14 within the iris 62 of the eye 52 (see FIG. 3). Alternatively, reflective device 14 can be implanted deep within the corneal stroma 64 (see FIG. 4). Placement in either of these locations provides the desired effect.

It has been found to be beneficial in this application to use a mirror for reflective device 14. This has the advantages of being biocompatible and inexpensive. Further, it is an efficient device for reflecting radiant energy. The mirror may be any suitable size, however, it has been found advantageous to limit the size of the mirror in length and width from about 20 microns to about 3 millimeters, and more preferably, to not more than 30 microns.

In use, radiant energy source 12 generates polarized beam 54, which is directed into the eye 52. If reflective device 14 is implanted in the iris 62, polarized beam 54 travels through cornea 56 and the aqueous humor 58 and is reflected off implanted reflective device 14. Reflected beam 60 travels back through the aqueous humor 58 and cornea 56 of the eye and is received by receiver system 18. Alternatively, if reflective device 14 is implanted in the corneal stroma 64, polarized beam 54 travels through cornea 58 and is reflected off implanted reflective device 14. Reflected beam 60 travels back through the cornea 56 and is received by receiver system 18. Based upon the optical rotation or refraction of reflected beam 60 as detected by detector 24, the glucose concentration, or the concentration of another substance within the body, is calculated by processor 26 as described above.

By virtue of the foregoing, there is thus provided a relatively inexpensive device and method for testing an animal for the existence of a biomedical disorder or condition using radiant energy, such as near-infrared radiation or polarized radiation, which reflected off an implanted reflective device, While the present invention has been illustrated by a description of two embodiments, it is not the intention of the applicant to restrict or limit the scope of the appended claims to such detail, Additional advantages will readily appear to those skilled in the art; thus, the invention is not limited to the specific details, apparatus or methods shown and described.

What is claimed is:

1. A system for use in testing for the existence of a biomedical disorder or condition using radiant energy comprising:

a source of radiant energy for projecting radiation into and through the tissue of a portion of an animal test subject;

a reflective device configured and sized for implantation in the body of the animal test subject for reflecting said incident radiation out of the body; and a receiver including a detector for detecting said reflected radiation and a processor in communication with said detector for calculating changes in said detected radiation relative to said incident radiation caused by the passage of said incident radiation through the body of the animal test subject to determine the existence of a biomedical condition or disorder.

2. The testing system of claim 1 wherein said reflective device is a mirror.

3. The testing system of claim 2 wherein said source of radiant energy projects a polarized beam of radiation.

4. The testing system of claim 3 wherein said mirror has a length and a width from about 20 microns to about 3 millimeters.

5. The testing system of claim 3 wherein said mirror has a length and width from about 20 microns to about 30 microns.

6. The testing system of claim 2 wherein said source of radiant energy projects a beam of near-infrared radiation.

7. The testing system of claim 6 wherein said mirror has a length and width of from about 100 micrometers to about 1 centimeter.

8. A system for use in measuring the glucose level of an animal comprising:
- a source of polarized radiant energy for projecting a beam of incident polarized radiation into and through the tissue of a portion of the body of an animal test subject;
- a reflective device configured and sized for implantation in the body of the animal for reflecting said incident polarized radiation out of the body; and
- a receiver including a detector for detecting said reflected radiation and a processor in communication with said detector for calculating the index of refraction of said detected radiation relative to said incident radiation to determine the glucose level of the animal.

9. The glucose monitoring system of claim 8 wherein said polarized radiation source is positioned to project said beam of incident polarized radiation into the eye of the animal and said reflective device is configured and sized to be implanted in the eye of the animal and positioned to reflect said incident radiation out of the eye.

10. The glucose monitoring system of claim 8 wherein said polarized radiation source is positioned to project said beam of incident polarized radiation into the eye of the animal and said reflective device is configured and sized to be implanted in an area of the eye of the animal selected from the group consisting of the anterior chamber, the iris and the corneal stroma, and positioned to reflect said incident radiation out of the eye.

11. A system for use in measuring the glucose content of the aqueous humor of an eye comprising:
- a polarizing crystal for projecting a beam of polarized radiation through the cornea and aqueous humor of an eye;
- a mirror configured and sized for implantation in the anterior chamber of the eye for reflecting said polarized beam of radiation back through the aqueous humor and cornea of the eye; and
- a receiver including a detector for detecting said reflected radiation and a processor in communication with said detector for calculating the optical rotation of said detected radiation relative to said incident radiation to determine the glucose level of the aqueous humor.

12. A system for use in measuring the presence and concentration of selected compounds in a body of an animal test subject using near-infrared radiant energy comprising:
- a source of near-infrared energy for projecting incident radiation into and through the tissue of a portion of the body of an animal test subject;
- a reflective device configured and sized for implantation in the body of the animal and for reflecting said incident radiation out of the body;
- a receiver including a detector for detecting said reflected radiation and a processor in communication with said detector for calculating changes in said detected radiation relative to said incident radiation to determine the presence and concentration of selected compounds in the body.

13. A method for measuring the glucose level of an animal comprising:
- providing a source of polarized radiation;
- providing a reflective device implanted within the body of an animal test subject;
- providing a receiver;
- projecting a polarized beam of radiation into and through the tissue of a portion of the body of an animal test subject with said external source of polarized radiation;
- reflecting said polarized beam of radiation off said implanted reflective device; and
- receiving said reflected radiation with said receiver and calculating the optical rotation thereof to measure the glucose level of the animal test subject.

14. A method for measuring the glucose content of the aqueous humor of an eye comprising:
- providing a source of polarized radiation;
- providing a mirror implanted in the anterior chamber of an eye, said mirror having a length and width of from about 20 microns to about 3 millimeters;
- providing a detector;
- projecting a beam of polarized radiation with said external source of polarized radiation through the cornea and aqueous humor of an eye;
- reflecting said polarized radiation off said implanted mirror; and
- detecting said reflected radiation with said detector and calculating the optical rotation of said reflected radiation thereby measuring the glucose content of the aqueous humor.

15. A method for measuring the glucose content of the aqueous humor of an eye comprising:
- providing a source of polarized radiation;
- providing a mirror implanted in the iris of the eye;
- providing a detector;
- projecting a beam of polarized radiation with said external source of polarized radiation through the cornea and aqueous humor of an eye;
- reflecting said polarized radiation off said implanted mirror; and
- detecting said reflected radiation with said detector and calculating the optical rotation of said reflected radiation thereby measuring the glucose content of the aqueous humor.

16. A method for measuring the glucose content of the cornea of an eye comprising:
- providing a source of polarized radiation;
- providing a mirror implanted in the corneal stoma of the eye;
- providing a detector;
- projecting a beam of polarized radiation with said external source of polarized radiation through the cornea of an eye;
- reflecting said polarized radiation off said implanted mirror; and
- detecting said reflected radiation with said detector and calculating the optical rotation of said reflected radiation thereby measuring the glucose content of the cornea.

17. A method for detecting the existence of a biomedical condition or disorder comprising:
- providing a source of radiant energy;
- providing a reflective device implanted in the eye of an animal test subject;

providing a receiver;

projecting a beam of radiant energy with said external source of radiant energy into the eye of the animal test subject;

reflecting said beam of radiant energy off said implanted reflective device; and receiving said reflected beam of radiant energy with said receiver and calculating changes in said detected radiation relative to said projected radiation caused by the passage of said projected radiation through the eye of the animal test subject to determine the existence of a biomedical condition or disorder.

18. A method for detecting the existence of a biomedical condition or disorder comprising:

providing a source of near-infrared radiant energy;

providing a reflective device implanted within the body of an animal test subject;

providing a receiver;

projecting a beam of near-infrared radiant energy with said external source of near-infrared radiant energy into and through the body of the animal test subject;

reflecting said beam of near-infrared radiant energy off said implanted reflective device; and receiving said reflected beam of near-infrared radiant energy with said receiver and calculating changes in said detected radiation relative to said incident radiation to determine the existence of a biomedical condition or disorder.

19. A method for detecting the presence and concentration of selected compositions in the body of an animal test subject comprising:

providing a source of radiant energy;

providing a reflective device implanted in the body of an animal test subject;

providing a receiver;

projecting a beam of radiant energy with said external source of radiant energy into and through the body of the animal test subject;

reflecting said beam of radiant energy off said implanted reflective device; and receiving said reflected beam of radiant energy with said receiver and calculating the change in said detected radiation relative to said incident radiation to determine the presence and concentration of selected compositions in the body of the animal test subject.

\* \* \* \* \*